| United States Patent [19] | [11] | 4,410,738 |
|---|---|---|
| Cordier | [45] | Oct. 18, 1983 |

[54] PREPARATION OF META-CHLOROPHENOLS BY SELECTIVE HYDRODECHLORINATION OF POLYCHLOROPHENOLS

[75] Inventor: Georges Cordier, Francheville, France

[73] Assignee: Rhone-Poulenc Industries, Paris, France

[21] Appl. No.: 332,740

[22] Filed: Dec. 21, 1981

[30] Foreign Application Priority Data

Dec. 24, 1980 [FR] France ............................. 80 27937

[51] Int. Cl.$^3$ ............................................. C07C 39/24
[52] U.S. Cl. ................................... 568/774; 568/716; 568/745; 568/746
[58] Field of Search ................ 568/774, 745, 746, 716

[56] References Cited

U.S. PATENT DOCUMENTS

| 2,803,669 | 8/1957 | Brainerd et al. | 568/774 |
|---|---|---|---|
| 3,912,782 | 10/1975 | Kiel et al. | 568/774 |
| 3,912,783 | 10/1975 | Wedemeyer et al. | 568/774 |
| 4,060,562 | 11/1977 | Wedemeyer et al. | 568/774 |

*Primary Examiner*—Werren B. Lone
*Attorney, Agent, or Firm*—Burns, Doane, Swecker & Mathis

[57] ABSTRACT

Meta-chlorophenols useful as intermediates in various organic syntheses are prepared by selectively catalytically hydrodechlorinating a polychlorophenol in liquid phase in an acid solvent medium which is at least partially aqueous, in the presence of a Group VIII noble metal catalyst and at least one Group 1b to 5a heavy metal, said polychlorophenol bearing chlorine substituents in both the meta- and ortho- and/or para-positions.

29 Claims, No Drawings

PREPARATION OF META-CHLOROPHENOLS BY SELECTIVE HYDRODECHLORINATION OF POLYCHLOROPHENOLS

CROSS-REFERENCE TO RELATED APPLICATIONS

My copending applications, Ser. No. 332,846 and Ser. No. 332,833, both filed concurrently herewith; and both assigned to the assignee hereof.

BACKGROUND OF THE INVENTION

1. Field of the Invention

The present invention relates to the preparation of phenols containing a nuclear chlorine substituent in at least one of the meta-positions relative to the phenolic hydroxyl function, and, more especially, to the preparation of such meta-chlorophenols via the hydrodechlorination of the more highly chlorinated chlorophenols.

As utilized and intended herein, the expression "meta-chlorophenols" will hereafter connote phenols bearing a chlorine atom substituent in at least one of the meta-positions.

The meta-chlorophenols, and in particular 3-chlorophenol and 3,5-dichlorophenol, are compounds which are of very great industrial value as intermediates in various organic syntheses.

2. Description of the Prior Art

A plurality of methods for the preparation of the meta-chlorophenols have heretofore been proposed to this art. Methods for generating the phenol group in chlorine-substituted aromatic compounds (for example, by alkaline hydrolysis of polychlorobenzenes, or by nitration of 3-chlorobenzene and 3,5-dichlorobenzene, followed by the reduction of the nitro group to an amino group, the diazotization of the latter and ultimate decomposition of the diazonium salt), methods for chlorinating polychlorophenols are particularly exemplary. The latter method is of very great industrial value because of the availability of the polychlorophenols, certain of which are conventional compounds, while others are by-products of limited value, which it is important to utilize.

Thus, for example, isomeric trichlorophenols and tetrachlorophenols, some of which contain one or two chlorine atoms in the meta-position relative to the phenolic hydroxyl, are obtained during the preparation of 2,3,4,6-tetrachlorophenol and pentachlorophenol by chlorinating 2,6-dichlorophenol, which is a by-product from the preparation of 2,4-dichlorophenol. These various polychlorophenols constitute preferred starting materials for the preparation of meta-chlorophenols by dechlorination. One method for removing the excess chlorine atoms consists of subjecting the polychlorophenols to hydrogenation in the vapor phase or in the liquid phase, in the presence of a catalyst. For reasons of simplicity, the expression "hydrodechlorination" will hereafter connote the dechlorination of polychlorophenols by hydrogenation.

The crux of the problem presented by the hydrodechlorination of polychlorophenols to yield 3-chlorophenol or 3,5-dichlorophenol is the selective removal of the chlorine atoms in the 2- and/or 4- and/or 6-positions relative to the phenolic hydroxyl. Various processes for the hydrodechlorination of polychlorophenols have been proposed, but to date none has proved fully satisfactory.

Thus, U.S. Pat. No. 2,803,669 features a process for the hydrodechlorination of polychlorophenols in the vapor phase, by passing a gaseous mixture of hydrogen and polychlorophenols over a catalyst based on cuprous halides (for example, cuprous chloride) deposited on alumina, the catalyst being maintained at highly elevated temperature (350° to 550° C.). When applied to the hydrodechlorination of 2,3,4,6-tetrachlorophenol, this process does not permit of the selective removal of the chlorine atoms in the 2-, 4- and 6-positions relative to the phenolic hydroxyl function. Indeed, the reaction mixture resulting from the hydrogenation essentially consists of 2,4-dichlorophenol and 2,6-dichlorophenol.

And French Patent Application No. 73/43,484, published under No. 2,209,738, proposes a process for the preparation of meta-halogenophenols by dehalogenating polyhalogenophenols by hydrogenation in the liquid phase at an elevated temperature, in the presence of a catalyst comprising either one or more sulfides or polysulfides of iron, nickel or cobalt, or a noble metal, such as palladium or platinum, associated with a sulfur derivative. The reaction is preferably carried out in the presence of a base, such as alkali metal hydroxides or carbonates, in order to neutralize the hydracids generated by the reaction, as they are formed. Although this process is shown to be very selective with respect to the formation of meta-chlorophenols, it displays the distinct disadvantage in that it must be carried out in the presence of a base, and in particular an alkali metal base, under temperatures (the temperature must preferably be between 180° and 330° C.) which favor the formation of halogenodioxins, and in particular of polychlorodioxins, certain of which are known to be highly toxic. In practice, a disadvantage of this type renders the process devoid of any meaningful industrial value. Thus, serious need exists in this art for a selective process for obtaining meta-chlorophenols via the hydrodechlorination of polychlorophenols, which process would obviate the need for the presence of alkali metal bases.

SUMMARY OF THE INVENTION

Accordingly, a major object of the present invention is the provision of an improved process for the selective hydrodechlorination of polychlorophenols, which improved process is conspicuously devoid of those disadvantages and drawbacks immediately above outlined.

Briefly, the present invention features a process for selectively preparing chlorophenols bearing a chlorine atom substituent in at least one of the meta-positions relative to the phenolic hydroxyl group, by the hydrogenation, under the influence of heat, in the liquid phase, and in the presence of a catalyst based on a noble metal of Group VIII of the Periodic Table, of polychlorophenols having the structural formula (I):

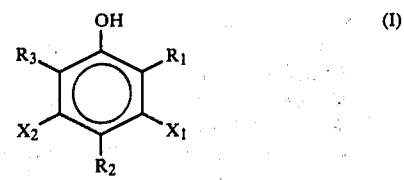

in which: $X_1$ and $X_2$, which are identical or different, each represents a chlorine atom, a hydrogen atom or an alkyl, aryl, arylalkyl, alkoxy or aryloxy radical, at least one of the symbols $X_1$ and $X_2$ representing a chlorine atom, and $R_1$, $R_2$ and $R_3$, which may also be identical or different, each represents a chlorine atom, a hydrogen atom, an alkyl radical, an aryl or arylalkyl radical or an alkoxy or aryloxy radical, at least one of the symbols $R_1$, $R_2$ and $R_3$ representing a chlorine atom, and said hydrodechlorination being characterized in that it is carried out in an acid solvent medium which is at least partially aqueous, in the presence of at least one Group 1b, 2b, 3a, 4a or 5a heavy metal of the Periodic Table [compare R. C. Weast, *Handbook of Chemistry and Physics*, 53rd Edition (1972–1973)].

DETAILED DESCRIPTION OF THE INVENTION

More particularly according to this invention, in the formula (I), those radicals $X_1$, $X_2$, $R_1$ and $R_3$ which do not symbolize a chlorine atom represent more advantageously an alkyl radical containing from 1 to 10 carbon atoms and preferably from 1 to B 4 carbon atoms, such as methyl, ethyl, n-propyl, isopropyl, n-butyl, isobutyl or t-butyl radicals, a phenyl radical, a benzyl radical, an alkoxy radical containing from 1 to 10 and preferably from 1 to 4 carbon atoms, such as methoxy, ethoxy, n-propoxy, isopropoxy or n-butoxy radicals, or the phenoxy radical.

The solvent medium in which the reaction is carried out can exclusively consist of water, or of a mixture, in all proportions, of water and one or more organic solvents which are liquid and inert under the conditions of reaction. It is not necessary for this solvent or these solvents to be miscible with water; their function consists essentially in dissolving the polychlorophenols. Examples of solvents which are representative are: aliphatic hydrocarbons such as octane and hexane, cycloaliphatic hydrocarbons such as cyclohexane, aromatic hydrocarbons such as benzene, toluene and xylenes, and aromatic chlorohydrocarbons such as monochlorobenzene and polychlorobenzenes.

Among these solvents, monochlorobenzene and the polychlorobenzenes are of particular value.

Essentially because of their boiling points, it is more preferable to use dichlorobenzenes and trichlorobenzenes if the solvent medium for the reaction consists of a mixture of water and organic solvent.

The volume ratio water/organic solvent is not critical; the water can represent, for example, from 5% to 100% of the total volume of the solvent medium. Most advantageously, the water constitutes from 50 to 100% of the total volume of the solvent medium.

For convenience, the term "aqueous solution" will hereafter be used to connote the solvent medium in which the reaction is carried out, but it should be clearly understood that this term also includes the solutions based on water/organic solvent mixtures such as defined above. The concentrations of the various compounds will be expressed, not relative to the water alone, but relative to the overall volume of the solvent medium.

The acidity of the medium can vary over wide limits. Preferably, the concentrations of protons in the aqueous solution is at least 0.5 $H^+$ ion per liter. There is no critical upper limit for this concentration, although excessive acidity of the reaction medium is not desirable, such that corrosion of the apparatus will be curtailed. Typically, the concentration of protons does not exceed 15 $H^+$ ions per liter and preferably does not exceed 8 $H^+$ ions per liter.

The acid aqueous medium in which the hydrogenation is carried out consists of an aqueous solution of a strong mineral acid, such as sulfuric acid and phosphoric acid, and hydracids, in particular hydrochloric acid, hydrobromic acid and hydriodic acid. It is preferred to use the latter acids because it has been found that the presence of halide ions exerts a favorable influence on the course of the reaction. In practice, aqueous solutions of hydrochloric acid are used because hydrochloric acid is formed during the hydrodechlorination. However, it is nonetheless possible, without departing from the scope of the invention, to commence the hydrogenation in the absence of hydrochloric acid, the latter being developed in the reaction medium by the hydrodechlorination reaction itself. It is also possible to use, as the acid aqueous medium containing halide ions, an aqueous solution of a strong halogenated or non-halogenated mineral acid and of at least one compound releasing halide ions, preferably chloride ions, such as alkali metal and alkaline earth metal halides, ammonium halides, quaternary ammonium halides and amine hydrohalides. In such a case, it is preferable to use alkali metal chlorides (in particular, sodium chloride and potassium chloride). The concentration of halide ions can also vary over wide limits, depending upon the nature of the halogen. Thus, if the halide present in the reaction medium is iodide, the concentration of $I^-$ ions can be as low as $1.10^{-4}$ ion/liter and preferably at least $1.10^{-2}$ $I^-$ ion/liter; if the halide is bromide, the concentration of bromide ions is at least $1.10^{-2}$ $Br^-$ ion and preferably at least 0.1 $Br^-$ ion per liter. In the case where the halide ion is the chloride ion, the concentration of $Cl^-$ ions per liter is at least 2 and preferably at least 4. Whatever the halide present in the reaction medium, there is no critical maximum value for the concentration of halide ions; however, for practical reasons, it is not necessary to exceed a concentration of 15 and preferably 8 g ions/liter. If hydracids are used as compounds for providing the halide ions, it may prove necessary to provide additional acidity if the concentration of hydracid is insufficient to adjust the concentration of protons in the aqueous solution within the above-mentioned limits. In this case, a strong mineral acid such as sulfuric acid is used conjointly. As outlined hereinabove, the process according to the invention is preferably carried out in aqueous solutions of hydrochloric acid having a concentration equal to at least 2 mols of HCl per liter; more preferably, the concentration of the aqueous solutions of hydrochloric acid is between 2 and 8 mols of HCl per liter.

Bismuth, lead, tin, thallium, mercury and silver are exemplary, in particular, of those heavy metals which are suitable for carrying out the process according to the present invention. Silver and tin are very particularly advantageous.

The heavy metals can be employed in the metallic form or in the form of derivatives thereof which are soluble in the acid aqueous phase and in which the radical combined with the metal is not critical. Thus, it is possible to employ oxides, salts of mineral or organic acids, or metal chelates or complexes. In practice, salts of mineral acids, and in particular halides, are more preferably employed. The following are non-limiting examples of suitable metal salts which can be used: stannous chloride, stannic chloride, silver nitrate, thallous chloride, thallic chloride, bismuth sulfate and lead sulfate. Because of the reducing nature of the reaction medium, it has proved preferable to use the heavy metals in their metallic state. For this purpose, the catalyst used is a catalyst obtained by the co-precipitation of a noble metal and at least one of the above-mentioned heavy metals, by reducing an aqueous solution of their corresponding salts by conventional technique, preferably in the presence of a support.

The amount of heavy metal employed can also vary over wide limits, depending upon the form in which it is used. If the heavy metal is present in the metallic state in the catalyst based on a noble metal, the amount thereof is calculated such that the ratio of the number of gram atoms of heavy metal to the number of gram atoms of noble metal is at least 0.3. There is no critical upper limit to the value of this ratio, but it need not exceed 10. Preferably, this ratio ranges from 0.6 to 2. If the heavy metal is employed in the form of a derivative thereof which is soluble in the acid aqueous phase, the amount of such derivatives must be sufficient for the amount of metal available at the active sites of the catalyst based on a noble metal to ensure that the reaction proceeds satisfactorily. In this case, this amount is calculated such that the concentration of metal cations in the acid aqueous phase is at least $1.10^{-4}$ g ion/liter of heavy metal and preferably at least $1.10^{-2}$ g ion/liter. There is no critical upper limiting value for this concentration, but for obvious practical reasons, the solubility limits of the metal derivative should not be exceeded.

The noble metals upon which the catalysts utilized per the invention are based, are mainly metals of Group VIII of the Periodic Table, such as ruthenium, rhodium, palladium, osmium, iridium and platinum. Palladium is the preferred metal. The metal can be in the pure metallic state or in the form of chemical compounds thereof; in general, the metal is preferably used in the metallic form because, under the operating conditions of reaction, compounds tend to be reduced to their metallic state. The catalyst can either be supported or unsupported. Any inert support which is itself known can be used as the catalyst support; more particularly suitable supports which are exemplary are carbon black, silica and barium sulfate; carbon black is a preferred support. The catalyst and its support are advantageously in a finely divided form; specific surface areas of more than 100 m$^2$/g are generally suitable.

The amount of catalyst used is such that the proportion by weight of noble metal of the catalyst, relative to the compound of the formula (I) to be treated, typically ranges from 0.01 to 10% and preferably from 0.1 to 5%.

The reaction temperature typically ranges from 50° to 350° C. and preferably from 100° to 250° C.

The hydrogen partial pressure can also vary over wide limits and be greater than, less than or equal to atmospheric pressure. More specifically, the hydrogen pressure ranges from 0.1 to 60 bars and preferably from 0.5 to 50 bars. Pressures of more than 60 bars could indeed be used, but this does not result in any particular advantages. The total pressure at which the reaction is carried out essentially depends on the temperature conditions, the volatility, under these conditions, of the acid used and the degree of the hydrogen partial pressure. It is self-evident that the total pressure must be sufficient to maintain the reaction medium liquid and/or to maintain the concentration of acid in the aqueous phase within the aforenoted limits.

Exemplary of the polychlorophenols of the formula (I) which are useful starting materials in the process according to the present invention are: 2,3-dichlorophenol, 2,5-dichlorophenol, 3,4-dichlorophenol, 2,3,4-trichlorophenol, 2,3,6-trichlorophenol, 2,4,5-trichlorophenol, 2,3,5-trichlorophenol, 3,4,5-trichlorophenol, 2,3,4,6-tetrachlorophenol, 2,3,4,5-tetrachlorophenol, 2,3,5,6-tetrachlorophenol, pentachlorophenol, 2,3,4-trichloro-6-methylphenol, 2,3-dichloro-6-methylphenol, 2,3,4,6-tetrachloro-5-methylphenol, 2,3-dichloro-4-methylphenol, 2,3,5,6-tetrachloro-4-methylphenol, 2,5-dichloro-3,4-dimethylphenol, 2,5-dichloro-4-ethylphenol, 2,5-dichloro-4-propylphenol, 2,5-dichloro-4-t-butylphenol, 3,4,6-trichloro-2-benzylphenol, 3,4-dichloro-2-methoxyphenol, 3,6-dichloro-2-methoxyphenol, 4,5-dichloro-2-methoxyphenol, 5,6-dichloro-2-methoxyphenol, 3,4,6-trichloro-2-methoxyphenol, 3,4,5-trichloro-2-methoxyphenol, 3,4,5,6-tetrachloro-2-methoxyphenol, 4,5-dichloro-3-methoxyphenol, 5,6-dichloro-3-methoxyphenol, 2,5-dichloro-3-methoxyphenol, 4,5,6-trichloro-3-methoxyphenol, 2,3,6-trichloro-3-methoxyphenol, 4,5-dichloro-2-phenoxyphenol, 2,3,5,6-tetrachloro-4-phenoxyphenol, 3,4-dichloro-3-ethoxyphenol, 3,4,5-trichloro-2-ethoxyphenol, 3,4-dichloro-2-phenylphenol and 3,5,6-trichloro-2-phenylphenol.

In actual practice, the dichlorophenols and trichlorophenols are preferably used.

The following are exemplary of those phenols bearing a chlorine atom substituent in at least one of the meta-positions relative to the phenolic hydroxyl group, which are conveniently prepared by the process according to the present invention: 3-chlorophenol, 3,5-dichlorophenol, 3-chloro-6-methylphenol, 3-chloro-5-methylphenol, 3-chloro-4-methylphenol, 3,5-dichloro-4-methylphenol, 5-chloro-3,4-dimethylphenol, 3,5-dichloro-4-ethylphenol, 3,5-dichloro-4-propylphenol, 3,5-dichloro-4-t-butylphenol, 3-chloro-2-benzylphenol, 3-chloro-2-methoxyphenol, 3-chloro-6-methoxyphenol, 3,5-dichloro-2-methoxyphenol, 3-chloro-5-methoxyphenol, 3-chloro-6-phenoxyphenol, 3,5-dichloro-6-phenoxyphenol, 3-chloro-2-ethoxyphenol and 3-chloro-2-phenylphenol.

The process according to the invention can be carried out either continuously or batchwise. Upon completion of the reaction, the catalyst is filtered off and can be recycled as such into a further hydrodechlorination operation. The meta-chlorophenols formed can easily be separated from the reaction mixture by extraction with an organic solvent which is immiscible with water, and then recovered by distillation, after removal of the solvent of extraction.

In order to further illustrate the present invention and the advantages thereof, the following specific examples are given, it being understood that same are intended only as illustrative and in nowise limitative.

EXAMPLE 1

The following materials were introduced into a 250 ml tantalum-lined stainless steel autoclave equipped with a stirring system:

(i) 1 g of 3,4-dichlorophenol;

(ii) 100 ml of a 6 N aqueous solution of hydrochloric acid; and (iii) 0.210 g of a catalyst consisting of palladium deposited on an active charcoal having a specific surface area of 1,000 m$^2$.g$^{-1}$, and containing 2% by weight of palladium metal (namely, 4.2 mg of palladium) and 3% by weight of silver metal (namely, 6.3 mg of silver).

After the autoclave had been closed, its contents were heated to 190° C., hydrogen was then introduced until the total pressure attained a value of 45 bars, and these conditions were maintained for 5 hours, 50 minutes. The contents of the autoclave were subsequently cooled, degassed and then drawn off. The catalyst was then separated from the aqueous phase. The chlorophenols were extracted from the aqueous phase with 300 ml of ether. The catalyst was then separated from the aqueous phase. The chlorophenols were extracted from the aqueous phase with 300 ml of ether. The catalyst was washed 3 times with 20 ml of ether in order to extract the chlorophenols contained therein. The ether extracts were combined, the ether was then removed by distillation and the chlorophenols present in the distillation residue were determined and identified by vapor phase chromatography.

The results of the analysis reflected that all of the 3,4-dichlorophenol had been converted [degree of conversion (DC): 100%]. The following were identified in the distillation residue:

3-chlorophenol: yield relative to the 3,4-dichlorophenol introduced (RY)=72%
phenol: RY=28%.

EXAMPLE 2

Example 1 was repeated, but after having replaced the Pd/Ag catalyst by 0.14 g of a palladium-on-charcoal catalyst (5% by weight of palladium deposited on carbon black having a specific surface area of 1,000 $m^2.g^{-1}$), and the reaction was carried out in the presence of 0.19 g of stannous chloride.

After a reaction time of 6 hours at 190° C. under a total pressure of 43 bars, the contents of the autoclave were cooled and treated as in Example 1. The following results were obtained:
DC of 3,4-dichlorophenol=100%
RY of 3-chlorophenol=68%
RY of 4-chlorophenol=2.5%
RY of phenol=29.5%.

EXAMPLE 3

Example 1 was repeated, the following amounts of the following materials being introduced:
(i) 1 g of 2,5-dichlorophenol;
(ii) 0.3 g of Pd-on-charcoal containing 2% of palladium metal and 3% of silver metal (identical to that of Example 1); and
(iii) 100 ml of 6 N aqueous hydrochloric acid.

The reaction was carried out under the conditions of Example 1 for 5 hours.

After the same treatment as in Example 1, the following results were obtained:
DC of the 2,5-dichlorophenol: 87%
Y of 5-chlorophenol: 69%
Y of 2-chlorophenol: 14%
Y of phenol: 17%

EXAMPLE 4

Example 1 was repeated, the following amounts of the following materials being introduced:
(i) 1.6 g of pentachlorophenol ($6\times10^{-3}$ mols);
(ii) 0.3 g of Pd-on-charcoal containing 2% of palladium metal and 3% of silver metal (identical to that of Example 1); and
(iii) 100 ml of 6 N aqueous hydrochloric acid.

After a reaction time of 40 hours at 210° C. under a total pressure of 65 bars, the contents of the autoclave were cooled and treated as in Example 1.

The following results were obtained:
DC of the pentachlorophenol: 100%
RY of the 3,5-dichlorophenol: 83%
RY of the 2,3,5,6-tetrachlorophenol: 2.9%
RY of the 2,3,5-trichlorophenol: 4.8%
RY of the 3-chlorophenol: 9.3%

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims.

What is claimed is:

1. A process for the selective preparation of a meta-chlorophenol, comprising selectively catalytically hydrodechlorinating, with hydrogen, a polychlorophenol having the structural formula (I):

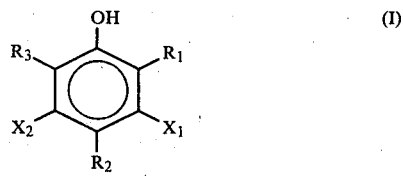

wherein $X_1$ and $X_2$, which may be identical or different, each represents a chlorine atom, a hydrogen atom or an alkyl, aryl, arylalkyl, alkoxy or aryloxy radical, at least one of $X_1$ or $X_2$ being a chlorine atom, and $R_1$, $R_2$ and $R_3$, which may also be identical or different, each represents a chlorine atom, a hydrogen atom, an alkyl, aryl, arylalkyl, alkoxy or aryloxy radical, at least one of $R_1$, $R_2$ or $R_3$ being a chlorine atom, and said selective catalytic hydrodechlorination being carried out at elevated temperatures in liquid phase in an acid solvent medium which is at least partially aqueous, in the presence of a Group VIII noble metal catalyst and at least one Group 1b, 2b, 3a, 4a or 5a heavy metal.

2. The process as defined by claim 1, wherein said at least partially aqueous acid solvent medium comprises a water/organic solvent mixture containing from 5 to 100% by volume of water.

3. The process as defined by claim 2, said water/organic solvent mixture containing from 50 to 100% by volume of water.

4. The process as defined by claims 1, 2, or 3, wherein said polychlorophenol having the structural formula (I) those radicals $X_1$, $X_2$, $R_1$, $R_2$ and $R_3$ which are not a chlorine atom represent an alkyl radical containing from 1 to 10 carbon atoms, a phenyl radical, a benzyl radical, an alkoxy radical containing from 1 to 10 carbon atoms or a phenoxy radical.

5. The process as defined by any of claims 1 to 3, wherein the concentration of protons in the aqueous acid solvent medium is at least 0.5 g ion/liter.

6. The process as defined by claim 5, wherein the concentration of protons in the aqueous acid solvent medium is at most 15 g ions/liter.

7. The process as defined by claim 6, wherein said aqueous acid solvent medium comprises halide ions.

8. The process as defined by claim 7, wherein the concentration of halide ions in the said aqueous acid solvent medium is at least $1.10^{-4}$ g ion/liter.

9. The process as defined by claim 8, wherein the concentration of halide ions in the said aqueous acid solvent medium is at most 15 g ions/liter.

10. The process as defined by claim 9, wherein said aqueous acid solvent medium comprises chloride ions.

11. The process as defined by claim 6, wherein said aqueous acid solvent medium comprises an aqueous solution of hydrochloric acid.

12. The process as defined by claim 11, wherein said aqueous solution of hydrochloric acid has a concentration of from 2 mols.liter$^{-1}$ to 8 mols.liter$^{-1}$.

13. The process as defined by claim 6, wherein said heavy metal is in the free metallic state.

14. The process as defined by claim 6, wherein said heavy metal is in the form of an inorganic or organic compound thereof which is soluble in said aqueous acid solvent medium.

15. The process as defined by claim 14, wherein said heavy metal is in the form of a chloride thereof.

16. The process as defined by claim 6, wherein said heavy metal is Bi, Pb, Sn, Tl, Hg or Ag.

17. The process as defined by claim 13, wherein said heavy metal is silver.

18. The process as defined by claim 14, wherein said heavy metal compound is stannous chloride.

19. The process as defined by claim 6, wherein said noble metal catalyst is palladium deposited on an inert support.

20. The process as defined by claim 19, wherein the amount of catalyst, expressed as the weight of noble metal per 100 g of polychlorophenol having the structural formula (I), ranges from 0.01 g to 10 g.

21. The process as defined by claim 13, wherein the amount of heavy metal is calculated such that the ratio of the number of gram atoms of said metal to the number of gram atoms of noble metal is at least 0.3.

22. The process as defined by claim 14, wherein the amount of heavy metal compound is calculated such that the concentration of heavy metal ions in the aqueous acid solvent medium is at least $1.10^{-4}$ g ion per liter.

23. The process as defined by claim 6, wherein the hydrodechlorination reaction temperature ranges from 50° to 350° C.

24. The process as defined by claim 23, wherein the hydrogen partial pressure ranges from 0.1 to 60 bars.

25. The process as defined by claim 24, wherein the polychlorophenol having the structural fomula (I) is a dichlorophenol or trichlorophenol bearing a chlorine atom substituent in at least one of the meta-positions relative to the phenolic hydroxyl group.

26. The process as defined by claim 25, wherein the polychlorophenol having the structural formula (I) is 3,4-dichlorophenol, 2,5-dichlorophenol or pentachlorophenol.

27. The process as defined by claims 1, 2 or 3, wherein said polychlorophenol having the structural formula (I) is 2,3-dichlorophenol, 2,5-dichlorophenol, 3,4-dichlorophenol, 2,3,4-trichlorophenol, 2,3,6-trichlorophenol, 2,4,5-trichlorophenol, 2,3,5-trichlorophenol, 3,4,5-trichlorophenol, 2,3,4,6-tetrachlorophenol, 2,3,4,5-tetrachlorophenol, 2,3,5,6-tetrachlorophenol, pentachlorophenol, 2,3,4-trichloro-6-methylphenol, 2,3-dichloro-6-methylphenol, 2,3,4,6-tetrachloro-5-methylphenol, 2,3-dichloro-4-methylphenol, 2,3,5,6-tetrachloro-4-methylphenol, 2,5-dichloro-3,4-dimethylphenol, 2,5-dichloro-4-ethylphenol, 2,5-dichloro-4-propylphenol, 2,5-dichloro-4-t-butylphenol, 3,4,6-trichloro-2-benzylphenol, 3,4-dichloro-2-methoxyphenol, 3,6-dichloro-2-methoxyphenol, 4,5-dichloro-2-methoxyphenol, 5,6-dichloro-2-methoxyphenol, 3,4,6-trichloro-2-methoxyphenol, 3,4,5-trichloro-2-methoxyphenol, 3,4,5,6-tetrachloro-2-methoxyphenol, 4,5-dichloro-3-methoxyphenol, 5,6-dichloro-3-methoxyphenol, 2,5-dichloro-3-methoxyphenol, 4,5,6-trichloro-3-methoxyphenol, 2,3,6-trichloro-3-methoxyphenol, 4,5-dichloro-2-phenoxyphenol, 2,3,5,6-tetrachloro-4-phenoxyphenol, 3,4-dichloro-3-ethoxyphenol, 3,4,5-trichloro-2-ethoxyphenol, 3,4-dichloro-2-phenylphenol or 3,5,6-trichloro-2-phenylphenol.

28. The process of claim 1, wherein the Group VIII metal is in a metallic state.

29. The process of claim 1, wherein the hydrodechlorination reaction temperature ranges from 50° to 350° C., and the hydrogen partial pressure ranges from 0.1 to 60 bars.

* * * * *